United States Patent
Utterberg (10) Patent No.: US 7,056,308 B2
(45) Date of Patent: Jun. 6, 2006

(54) MEDICAL DEVICE WITH ELASTOMERIC PENETRABLE WALL AND INNER SEAL

(75) Inventor: David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 28 days.

(21) Appl. No.: 10/613,922

(22) Filed: Jul. 3, 2003

(65) Prior Publication Data

US 2004/0073176 A1   Apr. 15, 2004

Related U.S. Application Data

(63) Continuation-in-part of application No. 10/264,863, filed on Oct. 4, 2002.

(51) Int. Cl.
*A61M 5/14*   (2006.01)
*A61M 37/00*   (2006.01)

(52) U.S. Cl. .......................................... 604/256; 604/86

(58) Field of Classification Search ............... 604/82, 604/83, 86, 87, 88, 89, 90, 91, 167.01, 167.02, 604/167.03, 167.04, 200, 201, 205, 244, 604/246, 256, 533, 534, 535, 536, 905; 137/845, 137/851; 251/149.1

See application file for complete search history.

(56) References Cited

U.S. PATENT DOCUMENTS

| | | | |
|---|---|---|---|
| 3,977,403 A | 8/1976 | Patel |
| 3,994,293 A | 11/1976 | Ferro |
| 4,000,739 A | 1/1977 | Stevens |
| 4,076,285 A | 2/1978 | Martinez |
| 4,105,187 A | 8/1978 | Huber |
| 4,128,098 A | 12/1978 | Bloom et al. |
| 4,143,853 A | 3/1979 | Abramson |
| 4,197,848 A | 4/1980 | Garrett et al. |
| 4,201,208 A | 5/1980 | Cambio, Jr. |
| 4,326,569 A | 4/1982 | Vaillancourt |
| 4,387,879 A | 6/1983 | Tauschinski |
| 4,512,766 A | 4/1985 | Vailancourt |
| 4,649,904 A | 3/1987 | Krauter et al. |
| 4,655,752 A | 4/1987 | Honkanen et al. |
| 4,673,400 A | 6/1987 | Martin |
| 4,752,287 A | 6/1988 | Kurtz et al. |
| 4,752,292 A | 6/1988 | Lopez et al. |

(Continued)

FOREIGN PATENT DOCUMENTS

CA   1248832   1/1989

(Continued)

OTHER PUBLICATIONS

Publication from ERCI: "Sharps Safety and Needle Stick Prevension"; pp. 95-108 (2001).

(Continued)

*Primary Examiner*—Kevin C. Sirmons
*Assistant Examiner*—Mark K Han
(74) *Attorney, Agent, or Firm*—Garrettson Ellis; Seyfarth Shaw LLP (57) ABSTRACT

A medical device has an interior for containment of fluids; an opening into the interior, and an elastomeric wall having at least one perforation. The wall comprises a fixedly placed, flexible barrier across the opening. The device also defines a passageway extending inwardly from adjacent to the elastomeric wall, the passageway being proportioned to receive and form an annular seal with a connector tube that extends into the interior through the perforation.

22 Claims, 5 Drawing Sheets

U.S. PATENT DOCUMENTS

| | | | |
|---|---|---|---|
| 4,758,225 A | 7/1988 | Cox et al. | |
| 4,765,588 A | 8/1988 | Atkinson | |
| 4,798,594 A | 1/1989 | Hillstead | |
| 4,809,679 A | 3/1989 | Shimonaka et al. | |
| 4,842,591 A | 6/1989 | Luther | |
| 4,874,377 A | 10/1989 | Newgard et al. | |
| 4,950,260 A | 8/1990 | Bonaldo | |
| 4,954,149 A | 9/1990 | Fullemann | |
| 4,981,469 A | 1/1991 | Whitehouse et al. | |
| 5,006,114 A | 4/1991 | Rogers et al. | |
| 5,041,097 A | 8/1991 | Johnson | |
| 5,060,812 A | 10/1991 | Ogle, II | |
| 5,061,253 A | 10/1991 | Yoshida | |
| 5,064,416 A | 11/1991 | Newgard et al. | |
| 5,100,394 A | 3/1992 | Dudar et al. | |
| 5,108,380 A | 4/1992 | Herlitze et al. | |
| 5,135,489 A | 8/1992 | Jepson et al. | |
| 5,188,620 A * | 2/1993 | Jepson et al. | 604/534 |
| 5,203,775 A | 4/1993 | Frank et al. | |
| 5,211,634 A | 5/1993 | Vaillancourt | |
| 5,215,538 A | 6/1993 | Larkin | |
| 5,242,393 A | 9/1993 | Brimhall et al. | |
| 5,242,432 A | 9/1993 | DoFrank | |
| 5,251,873 A | 10/1993 | Atkinson et al. | |
| 5,279,571 A | 1/1994 | Larkin | |
| 5,295,658 A | 3/1994 | Atkinson et al. | |
| 5,360,413 A | 11/1994 | Leason et al. | |
| 5,409,125 A | 4/1995 | Kimber et al. | |
| 5,417,673 A | 5/1995 | Gordon | |
| 5,441,487 A | 8/1995 | Vedder | |
| 5,456,675 A | 10/1995 | Wolbring et al. | |
| 5,470,319 A | 11/1995 | Mayer | |
| 5,501,426 A * | 3/1996 | Atkinson et al. | 251/149.1 |
| 5,533,708 A | 7/1996 | Atkinson et al. | |
| 5,540,661 A | 7/1996 | Tomisaka et al. | |
| 5,549,651 A | 8/1996 | Lynn | |
| 5,620,434 A | 4/1997 | Brony et al. | |
| 5,674,206 A | 10/1997 | Allton et al. | |
| 5,685,866 A | 11/1997 | Lopez | |
| 5,702,019 A | 12/1997 | Grimard | |
| RE35,841 E | 7/1998 | Frank et al. | |
| 5,957,898 A | 9/1999 | Jepson et al. | |
| 6,245,048 B1 | 6/2001 | Fangrow, Jr. et al. | |
| 6,261,282 B1 | 7/2001 | Jepson et al. | |
| 6,344,033 B1 | 2/2002 | Jepson et al. | |

FOREIGN PATENT DOCUMENTS

| | | |
|---|---|---|
| DE | 3303718 C1 | 10/1984 |
| WO | WO 91/05581 | 5/1991 |
| WO | WO 02/04065 A2 | 1/2002 |
| WO | WO 02/34326 | 5/2002 |

OTHER PUBLICATIONS

Photograph of JMS Connector with Planecta—Japanese Catalog Page.

Drawing Labeled Fresenius Connector.

\* cited by examiner

MEDICAL DEVICE WITH ELASTOMERIC PENETRABLE WALL AND INNER SEAL

This is a continuation-in-part of Utterberg, et al. application Ser. No. 10/264,863, filed Oct. 4, 2002.

BACKGROUND OF THE INVENTION

Tubing sets for the transfer of medical fluids such as blood or parenteral solution generally comprise flexible, plastic tubing with end connectors, which are often luer-type connectors. Injection sites are often carried on the tubing at the ends of, or between the ends of, the tubing sets, comprising an elastomeric diaphragm or bung which is carried in a housing in typically compressed or restrained fashion, so that a needle can resealably penetrate the elastomeric bung and communicate with the interior of the tubular set, for administration of medicines and the withdrawal of medical samples such as blood. Also, in the field of extracorporeal blood transport, in which blood is conveyed to and from an extracorporeal blood processing device such as a dialyzer or an aphaeresis apparatus, such an injection site may also be used to add parenteral solution such as normal saline.

Various ways have been proposed to make a connection through an elastomeric diaphragm injection site using a tube which is terminated in a male luer connector. The present means for doing this are cumbersome, see U.S. Pat. Nos. 5,242,393 and 6,344,033.

When an elastomeric wall is used as a diaphragm or bung for penetration by a needle or a male luer connector, it is desirable to aseptically clean the outer surface of the elastomeric wall before penetration with a needle or male luer (which penetrates through a preformed perforation in the elastomeric wall). To assure good, aseptic cleaning of the outer surface, the elastomeric wall can to be exposed in an outer position, open for lateral sweeping of an antiseptic-soaked pad or swab across its surface. This in turn raises a problem, in that there is a need for assuring reliable connection of a male luer, for example, residing in the elastomeric wall as it extends therethrough to provide fluid communication. Typical female luers comprise a sleeve having a conically tapered bore that matches the taper of the male luer, to provide a conical seal. However, if the elastomeric wall is positioned within such a sleeve, then it is difficult to swab. If it is exposed so as to be swabbable, then one has, up until now, been forced toward more expensive and cumbersome solutions of the problem.

In accordance with this invention, a simple system is provided for a fluid access device which can be connected with a male luer or other similarly extending connector tube, particularly an ISO standard male luer slip or luer lock connector, while providing for an added, internal seal that is applied when the male luer is connected and penetrating through the elastomeric wall. Thus, this simplified structure provides the desired outer exposure of the elastomeric wall, coupled with a good seal that resists accidental disconnection and leakage while the male luer or other connector tube is penetrating through the elastomeric wall.

DESCRIPTION OF THE INVENTION

In accordance with this invention, an injection site is provided as part of a medical device which has an interior for containment of a fluid (liquid or gas). For example, the medical device may be a drug vial or container which utilizes the injection site of this invention, or it can be a tubing set having a main flow path for blood, parenteral solution, gases, or the like, to permit access preferably either by a male luer (luer slip or luer lock) connector or other type of tubular probe, without any intermediate device as in the prior art, such access being to the flow path of the tube set or the interior of any other container. Preferably, access through the injection site is also available as well by a needle, sharp or blunt.

An opening is defined into the interior of the medical device, with an elastomeric wall forming a fluid/air tight barrier across said opening, preferably both at positive and negative pressures relative to atmosphere. The elastomeric wall typically defines a compressed, or at least constrained, sealed perforation extending at least nearly there through. This perforation may be a closed slit with one or many branches, as in the form of a star (*). It may comprise one or more curved slits, or a simple, straight slit. Optionally, a retaining skin or skins made of another material, or wall material, may prevent complete opening and passage of fluid through the perforation until desired. Also, typically, the elastomeric wall is compressed generally at its periphery, to cause pressurization of the perforation so that there is better sealing through the slit and some resistance to opening, as well as sealing to prevent tears around the elastomeric wall. Alternatively, it is possible to co-mold the elastomeric part and the housing parts in one operation, and in this and other instances the elastomeric wall will not be compressed at its periphery, since it will be held by the molded part in non-compressed but restrained condition. Also wall materials may preferably be used that exhibit cohesion or tackiness between the edges of the slit or perforation to hold it together in releasably closed position.

A retention wall may be provided, being generally rigid and nonelastomeric, and located to retain a peripheral portion of the elastomeric wall in its position. The peripheral portion of the elastomeric wall typically comprises an outer ring portion that is secured by the retention wall against an annular seat, with a central portion of the elastomeric wall being exposed to the exterior and said opening. A portion of the retention wall may be spaced from the elastomeric wall. The retention wall has a retention zone surrounding said opening, which zone is that part of the retention wall that engages (i.e. touches) and frictionally retains a connector tube, having a leading end, which is advanced into said opening to partially displace a central portion, and to open a flow aperture through, the elastomeric wall, for flow through said wall and connector tube. The flow aperture may be provided by a pre-formed perforation, or the connector tube may have a sharp point or edge to open the flow aperture by cutting through an elastomeric wall which does not have a perforation.

Alternatively, the retention wall may be placed spaced from the elastomeric wall, such that the elastomeric wall is first penetrated by the connector tube prior to engaging with the retention zone.

In some embodiments, the perforation may comprise a line having a length of about the outer diameter of a male ISO luer at a point adjacent to its minimum diameter end, which line can stretch to provide a desired 360 degree seal as the luer penetrates into the perforation. Such a system may be used with a luer slip or a luer lock system.

The elastomeric wall may be held by a retention member which receives the connector tube, and is dimensioned to grip the side wall of the connector tube with or without a stretched, displaced elastomeric wall intervening between the connector tube and the retention member.

It can also be seen that it may be possible to make connection through the injection site of this invention by conventionally using a hypodermic needle, where the sharp needle passes through the body of the elastomeric wall in normal piercing fashion, or through the at least partially preformed perforation such as a slit. When such a perforation or slip is used, it may be possible for a dull point needle to be used for connection.

Locking systems may be used as additional structure for connection, so that additional connector separation can be further eliminated as a risk.

Further by this invention, a medical device is provided having an interior for the containment or passage of fluids, an opening into the interior, and an elastomeric wall having at least one perforation. The wall comprises a fixedly placed, flexible barrier across the opening typically at an outer end thereof. The medical device, which may be for any of a large variety of purposes, also defines a passageway extending inwardly from adjacent to the elastomeric wall. At least part of the passageway may preferably be proportioned to receive, and form an annular seal with, a connector tube that is extended into the interior through said perforation.

This passageway may comprise an inwardly tapered bore which matches the taper of a male luer which projects through the elastomeric wall as the connector tube, so that a forward portion of the male luer engages by a frustoconical seal with the tapered wall of the passageway, to provide a seal that is similar to the conventional ISO standard luer seal. This seal comprises an annular seal with a portion of such a luer or other connector tube that extends into the interior of the medical device through the perforation.

Thus, one currently preferred aspect of this invention is to shift a seal between the medical device and a male luer or other connector tube from conventional positions that are outside of the elastomeric wall to a generally new position which is within the device and under the elastomeric wall. With such a seal being inside of the elastomeric wall, a simplified elastomeric wall can be used without major, extending skirts or other appendages as in much of the prior art, while such an elastomeric wall can be swabbed for aseptic cleaning, and good, reliable sealing and retention between the male luer and the medical device can still be achieved.

It may be desirable to supplement that seal with a conventional luer lock system. The design of this invention may provide a plurality of spaced ears or threads about the periphery, which can engage with the threads of an ISO male luer connector sleeve in a manner which is conventional, except as otherwise indicated herein.

The outer face of the elastomeric wall can be laterally exposed to the exterior to permit lateral swabbing, for aseptic cleaning prior to use. This may be accomplished by placing the elastomeric wall at an outer end of the opening of the medical device for lateral access. Alternatively, it might be accomplished with a slotted sheath extending outwardly from the elastomeric wall, with the slots providing lateral access to the outer surface of the elastomeric wall.

The device of this invention may define a bore portion positioned between the elastomeric wall and the passageway recited above. This bore portion may have an inner diameter which is larger than any inner diameter of the passageway, to provide an annular chamber that receives the material of the elastomeric wall when a connector tube is extending through the perforation. Then, as stated, the connector tube, typically a male luer, penetrates the perforation and forms an annular seal with the elastomeric wall. Preferably, below said bore portion, which in some embodiments is frustoconical as stated above, the male luer may also create an additional, annular seal with the passageway wall. The connector tube may have a frustoconical outer wall with an angle which substantially matches the frustoconical passageway wall, to facilitate the annular seal. Alternatively, the length and/or strength of the conical bond between the male luer and passageway wall may be reduced, if desired, by building in a slight difference in frustoconical angle between the two parts. Typically the angle in question approximates the angle of an ISO luer system, namely about 1–4° of all sides to the longitudinal axis of the bore.

The medical device of this invention may comprise a simple housing which is in connection with a length of flexible tubing, so as to be a component of a parenteral solution administration set, a blood handling set such as sets for blood collection or extracorporeal blood processing, or the like. The invention of this application may be modified to be used on an adapter of various kinds, a stopcock, or as a stopper in any kind of container or vial for typically medical materials. The device of this invention may be used with an essentially unlimited variety of medical devices, wherever aseptic access is desired. Thus, it may be carried on any kind of medical device, such as syringes, needles, fluid transport sets, including IV sets, blood tubing sets, blood bag sets, transfer sets, and winged needle sets. Also, the injection site of this invention may be carried on other medical devices such as medical fluid containers, body access devices, and VACUTAINER™ blood drawing units.

The access site of this invention, as part of such medical devices, may connect with a great number of different devices which carry a connector tube for connection with the access site of this invention. For example, the connector tube, such as a male luer, may be carried by a syringe barrel, a tube set, an adapter, a stopcock, a medical fluid container, a vial, or the like. It provides a sealed access system having an internal seal which is formed on connection with a male luer or the like, permitting in some embodiments the elastomeric wall to be laterally exposed to the exterior so that its outer surface can be swabbed with sterilizing antiseptic before use. Nevertheless, it is still capable of reliable connection, particularly with a male luer lock connector, or other, related designs.

DESCRIPTION OF SPECIFIC EMBODIMENTS

Figure 1:
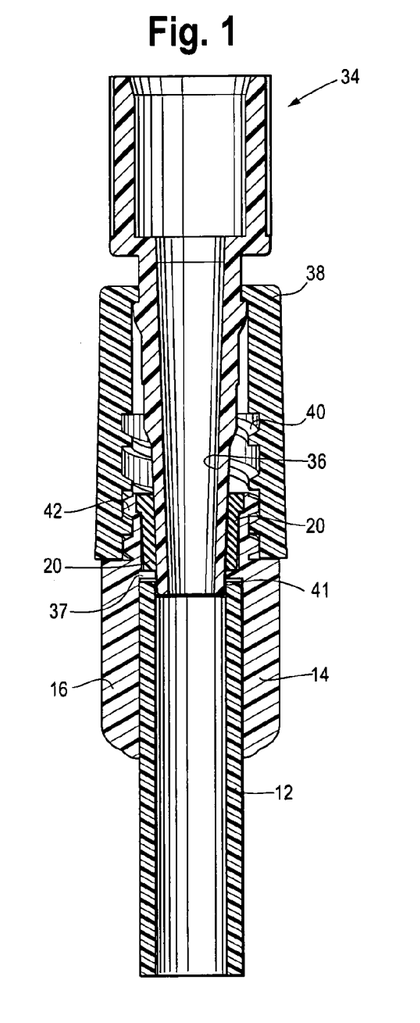
FIG. 1 is a longitudinal, sectional view of a portion of one embodiment of a tubing set, terminated with the injection site of this invention, shown to be in connection with a male luer lock connector.
Figure 1A:
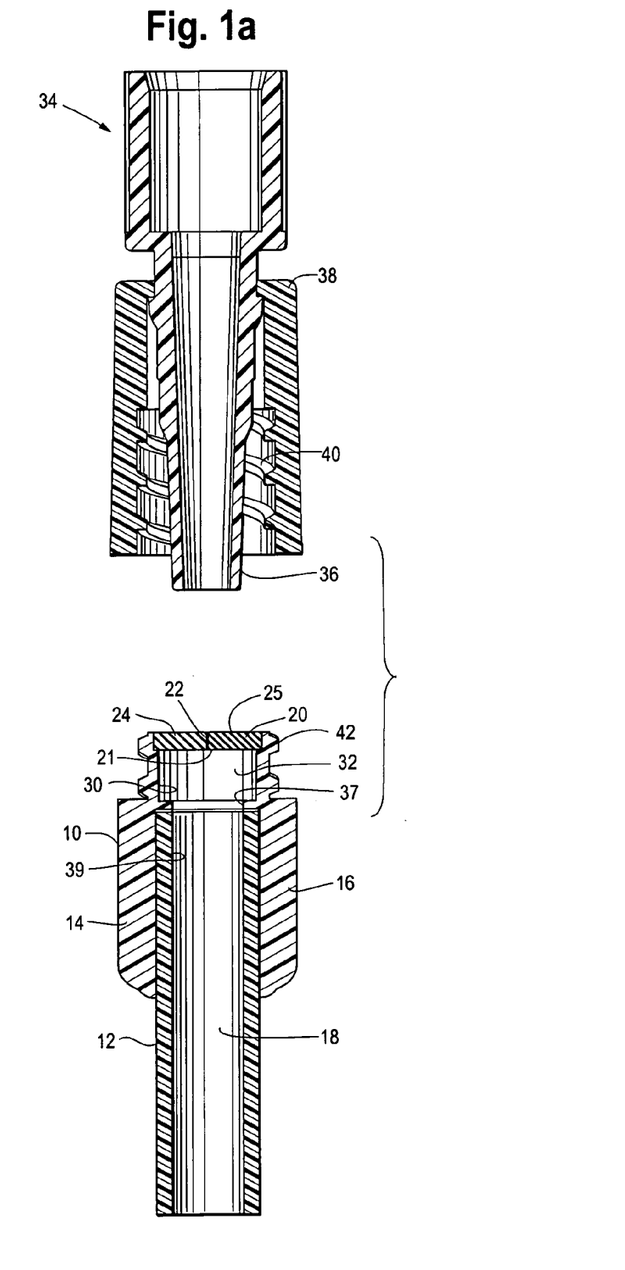
FIG. 1a is a similar view of another embodiment FIG. 1, with separated components.

Referring to FIGS. 1 and 1a, a medical device 10 is shown to comprise a length of flexible tubing 12, comprising part of a blood handling set, for example, having an end which is terminated in injection or access site 14.

Injection site 14 comprises a tubular housing 16 having a passageway 18 for containment of fluids, the inner wall of which comprises tubing 12. An elastomeric wall 20 is provided, which has a slit or perforation 22 to comprise a fixedly placed, flexible barrier across opening 21 to close off bore portion 32 and passageway 18. Elastomeric wall 20 is laterally secured at its periphery 24 at an end of housing 14 in a strong, sealing manner. It can be seen that the outer face 25 of elastomeric wall 20 is exposed to the exterior for access from lateral directions, to facilitate the use of an antiseptic-bearing swab, such as a commonly available isopropyl alcohol swab, to clean outer surface 25.

Passageway 18 may be separated from elastomeric wall 20 by a bore portion 32 defined by a lumen wall 30. Bore portion 32 has an inner diameter which may be larger than the inner diameter of passageway 18 in flexible tubing 12. The purpose of the larger diameter of passageway 32 is to receive stretched, deformed material of elastomeric wall 20 when a connector tube 36 of male luer lock connector 34 is extending through perforation 32, as shown in FIG. 1. Male luer connector 34 may be of conventional design and meeting ISO standards, comprising male luer component 36, having a frustoconical, tapered outer surface, and a rotatable locking ring 38 having internal threads 40. These may engage locking lugs 42 on injection site 14 in a conventional manner. Male luer 36 penetrates through perforation 22, as shown in FIG. 1. Perforation 22 may be a slit of less diameter than the diameter of male luer 36, so that male luer 36 stretches and deforms elastomeric wall 20 into the configuration shown in FIG. 1 as male luer 36 is advanced.

Elastomeric wall 20 is peripherally enclosed by a ring of material of housing 16, which ring also defines locking lugs 42. This peripheral retention of elastomeric wall 20 assists in the reclosing of slit 22 when the luer lock connector 34 is removed.

In one preferred embodiment of this invention the lesser diameter inner wall 37 and/or the inner wall 39 of tubing 12 can engage the outer wall of luer connector tube 36 at an annular seal area 41 to provide an inner, annular seal which is positioned below elastomeric wall 20, within housing 16. Thus, a removable, but double seal can be provided in this circumstance. A first seal is provided between male luer 36 and wall portions defining slit 22 of elastomeric wall 20. The second seal can be provided at area 41 between either or both of housing inner wall 37 and tubing inner wall 39, to provide additional sealing. The inner wall of tubing 12 may be of slightly less diameter, if desired, than the inner wall 37 of housing 14, with a compression seal forming as the resilient material of tubing 12 is pressed outwardly at area 41 by the advancing male luer 36.

Thus, the interior 18 of injection site 14 can be well protected from contamination as it is used more than once, since the outer face 25 of elastomeric wall 20 is accessible for wiping with an alcohol swab or the like, and a multiple seal is provided during the connection as shown in FIG. 1. The system readily recloses for further protection of the interior when male luer connector 34 is withdrawn. Thereafter, the outer face 25 may be treated again with an aseptic wipe, and reused for connection with another sterile male luer or luer connector.

Elastomeric wall 20 may be a disc of conventional elastomer used for such purpose, which is cut out of a sheet of the elastomer, for an efficient, mass production method for producing such elastomeric walls 20 at a cost which is substantially cheaper than molding, as may be required for many of the elastomeric, penetrable members used in prior art systems.

Figure 2:
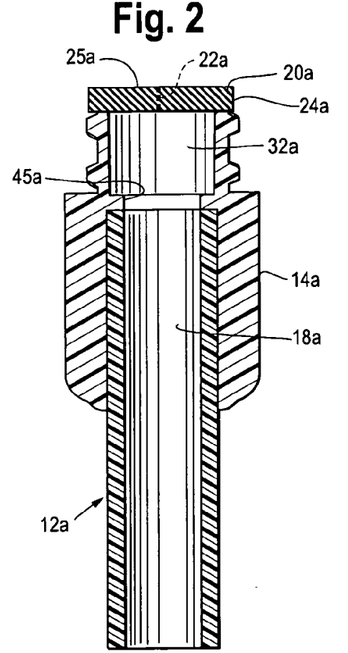
FIG. 2 is a longitudinal, sectional view of another embodiment of the tubing portion and injection site similar to that shown in FIG. 1.

FIG. 2 represents another embodiment of the invention, which is similar to the system of FIG. 1a, in which tubing 12a terminates in an injection or access site 14a. In this embodiment the perforated elastomeric wall 20a is attached at its periphery 24a to access site 14a, but only at the side thereof, and not at the actual, peripheral surface 24a as in the previous embodiment. In this embodiment, bore portion 32a is again provided, to permit a male luer or the like to pass through perforation 22a of elastomeric wall 20a, and to fold against the walls defining bore portion 32a, as in FIG. 1. Also, passageway 18a may be defined in part by a frustoconically tapered lumen wall 45a, spaced from elastomeric wall 20a by bore portion 32a. Frustoconical inner wall 45a of connector body 14a is preferably of a taper angle of about 1.72 degrees, to match the taper angle of a conventional male luer, and thus to form a conical seal with the male luer at a position underneath elastomeric wall 20a. This seal is like the known luer seal, to retain the two components together in releaseably locked and sealed relation, as bore portion 32a previously described, receives the expanded and deformed elastomeric wall 20a, comprising an annular chamber which retains the stretched and deflected portions of the elastomeric wall 20a, similar to that shown in FIG. 1, so that a smooth, sealed connection can be provided exhibiting characteristics of a conventional luer seal. Thus two seals are present against the male luer, the first one being provided by elastomeric wall 20a, and the second one comprising a conical friction seal resembling a luer seal at frustoconical wall 45a. At the same time, outer surface 25a of elastomeric wall 20a is well exposed for swabbing with antiseptic for aseptic cleaning prior to use.

As before, elastomeric wall 20a can be mass produced from appropriate elastomer sheeting by a process of punching out the discs of elastomer 20a, for a significant saving of manufacturing costs over molded, elastomeric walls.

Figure 3:
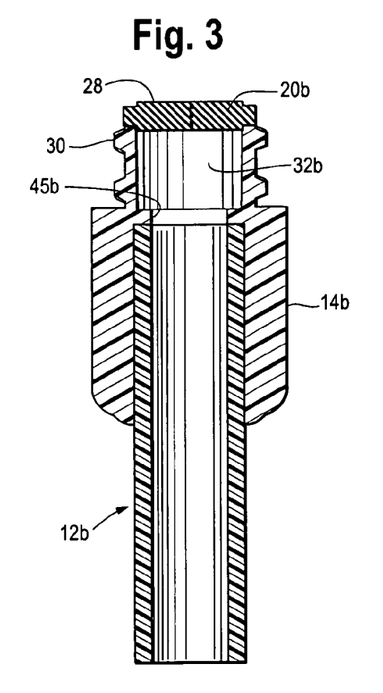
FIG. 3 is a longitudinal, sectional view of a tubing section and injection site similar to FIG. 2, but carrying a different design of elastomeric wall.

Turning to FIG. 3, an injection or access site 14b is shown, being similar in construction to the previous embodiments except as otherwise described herein. As before, flexible tubing 12b connects with the housing of the injection site 14b. Elastomeric wall 20b may carry a small outer ring 28 on its outer face, to help center a male luer which is to be pressed through elastomeric wall 20b. Second outer ring 30 also helps to center elastomeric wall 20b on the end of housing 14b during the manufacturing process. It can be seen that such an elastomeric wall is wider than it is long, and, like the previous embodiments, it lacks long projections, skirts, or appendages which extend downwardly into bore portion 32b. Such projections, skirts and appendages in certain analogous prior art devices operate in conjunction with a tube that is advanced into such systems. By the elimination of these, a simplification of manufacture and reduction of cost is achieved. Any such projections which are present are typically of a height or depth no greater than the thickness of elastomeric wall 20b, and preferably no more than about 3 millimeters. This is to facilitate swabbing of the outer surface, which could be interfered with if ring 28 is too high.

Figure 4:
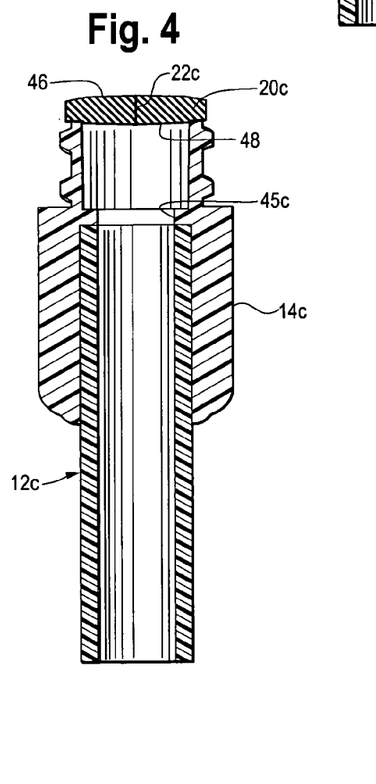
FIG. 4 is a longitudinal, sectional view of a tubing portion and another embodiment of the injection site of this invention similar to that of FIG. 2 but showing a third design of elastomeric wall.

Referring to FIG. 4, tubing 12c carries an injection or access site 14c, which is similar in design to the previous embodiments except for the nature of elastomeric wall 20c, which lacks rings 28, 30, and has convex sides 46, 48 to facilitate closing of perforation 22c under normal conditions.

Luer lock connector 34 is equally capable of making similar connections with the injection sites of FIGS. 2, 3 and 4 as it is with the injection site of FIGS. 1 and 1a. Also, a non-locking connector tube, particularly a male luer, can be used to seal with the tapered passageways 45a, 45b, or 45c in each embodiment, in the standard manner of a luer connection for added sealing underneath the respective elastomeric walls 20a, 20b, 20c.

Figure 5:
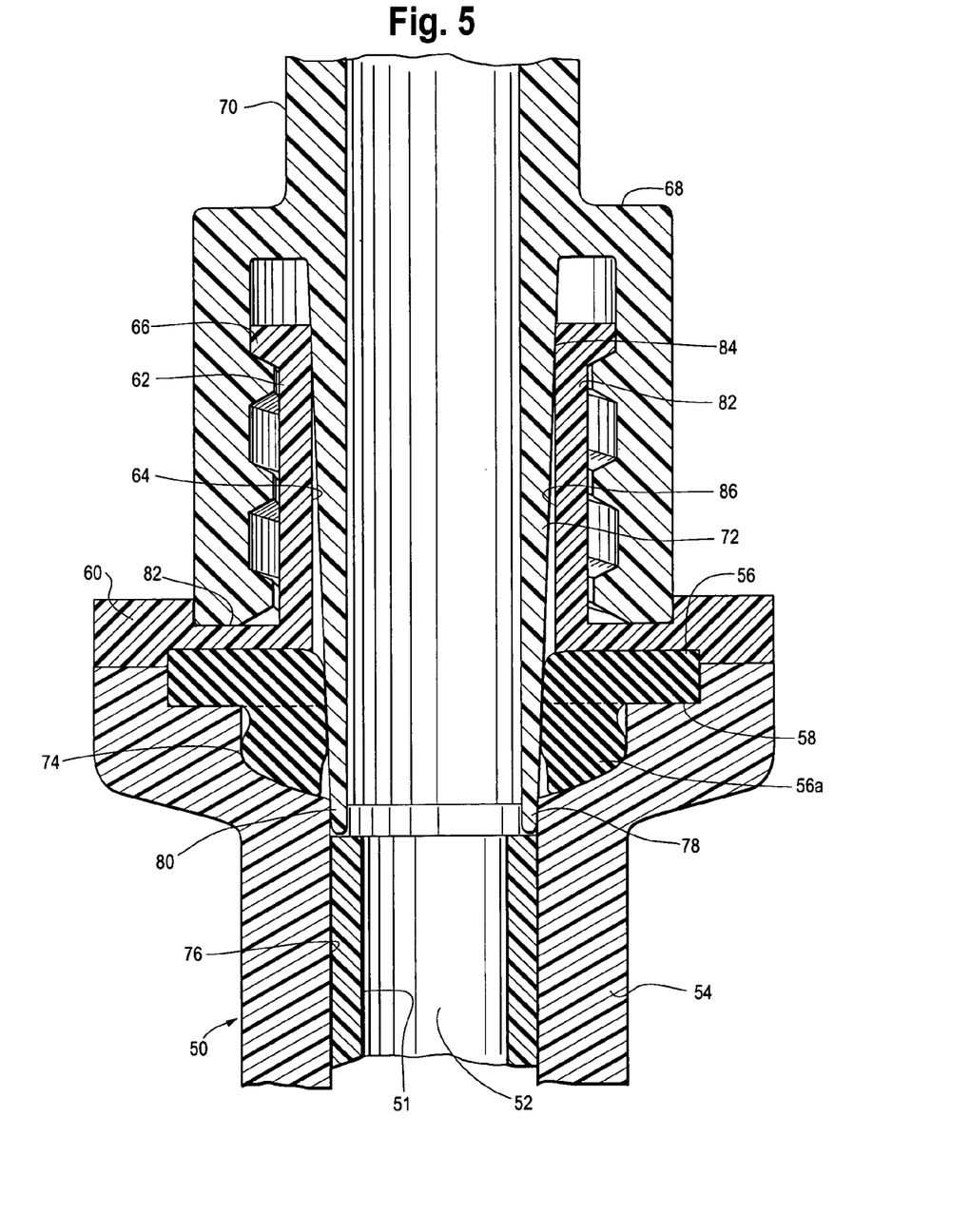
FIG. 5 is a longitudinal, sectional view of another design of injection site in accordance with this invention, adapted for connection on the end of flexible set tubing, and shown in connection with a male luer lock connector.

Referring to another embodiment, FIG. 5, another injection or access site 50 is carried on a medical device comprising a length of tubing 51 from a set or the like, and, as before, it has an injection site housing 54 with an interior 52 for containment or passage of fluids. Injection site housing 54 carries elastomeric wall 56, with the periphery thereof mounted on and glued or otherwise bonded by known adhesives or other methods to seat 58 and retained there by retention wall 60. Retention wall 60, in turn, defines a tubular connector member 62 which, in this embodiment, defines a cylindrical bore 64 and a plurality of lugs 66 to engage the locking sleeve 68 of a male luer lock connector 70, as shown. Male luer lock connector 70 may connect with tubing or any other desired medical device, with respect to where connection is desired with respect to device 50.

It can be seen that male luer 72 of luer lock connector 70 has advanced through tube 62 and has penetrated a perforation in elastomeric wall 56 to expand and deform said wall, and to pass into an enlarged diameter chamber 74, which provides room for the deflected portions 56a of elastomeric wall 56 as luer 72 is advanced.

In accordance with an aspect of this invention, male luer 72 advances so that its tip engages the wall 76 of passageway 52, to provide an annular seal 78 between wall 76 and the outer surface of end 80 of male luer 72 as luer 72 is advanced. From the viewpoint of a stationary position, the section of the luer at such a position increases in diameter as it advances, so that in a narrow, annular seal band 78 increasing pressures can be easily, manually applied to cause distortion of material of one or both of the parts forming seal 78. Such distortion improves the quality of the seal and provides a measure of resistance to disconnection, serving as a supplement for the accidental disconnection protection provided by locking ring 68.

Male luer 72 can be advanced until the lower edge 82 of locking ring 68 engages retention wall 60, or further, if the male luer is of the luer slip type that carries no locking ring having such a lower edge 82.

If locking ring 68 rotates and can move up and down, the distance that male luer 72 projects beyond end 82 of locking ring 68 can thus be adjusted, to adjust the depth of penetration of male luer 72.

In this embodiment, cylindrical wall 64 of connector tube 66 and male luer 72 can define between them an annular space 86 which is of variable thickness, larger at the bottom and non-existent at the top, because of the taper of the outer wall of luer 72. Thus, it can be seen that as luer 72 is advanced, another annular retention seal 84 may also be formed at the point along luer 72 where its outer diameter equals the inner diameter of cylindrical wall 64. This optional retention zone 84 will typically be near the outer end of connector tube 62 and the inner end of luer 72, and will comprise a narrow band of high-pressure connection, since it is a small area. There may be a distortion of material if luer 72 is advanced beyond the point of initial contact, to create a seal and retention zone between luer 72 and connector tube 62 along a relatively narrow band 84.

Thus, in the embodiment of FIG. 5 a triple seal of luer 72 may be provided (at areas 78, 84, and at elastomeric wall 56), along with good, added retention which may be provided by the arrangement of threaded locking ring 68 and ears 66.

Figure 6:
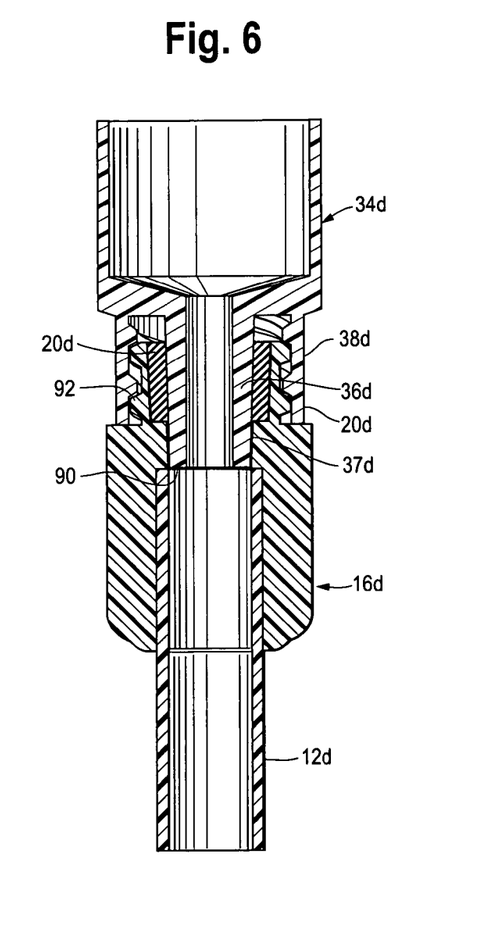
FIG. 6 is a longitudinal, sectional view of a tubing section and injection site similar to that of FIGS. 1 and 1a but showing a modified embodiment.
Figure 6A:
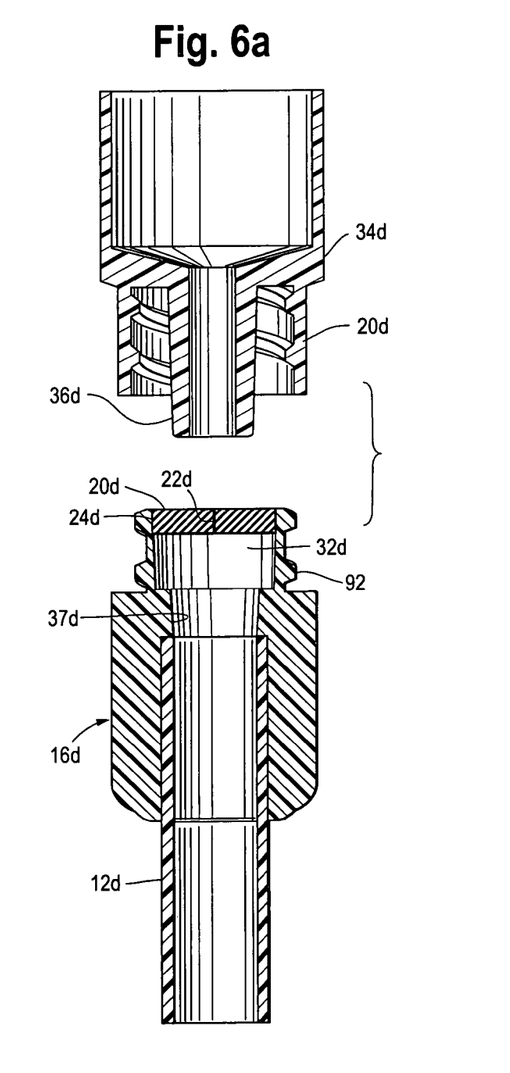
FIG. 6a is a similar view of FIG. 6, with separated components.

Referring to FIGS. 6 and 6a, this embodiment of injection or access site 16d is carried on flexible tubing 12d, and resembles the embodiment of FIG. 1a, with similar parts exhibiting similar functions. Elastomeric wall 20d can be seen to be retained and constrained at its periphery 24d to facilitate closing of slit 22d in a manner similar to that described in FIG. 1, when luer or luer lock connector 34d is withdrawn.

Enlarged bore portion 32d functions similar to bore portion 32, in that it provides room for displaced portions of elastomeric wall 20d as the luer 36d displaces it. Underneath bore portion 32d is a lesser diameter, inner tubular wall portion 37d, which is of greater length in the corresponding inner wall 37 of FIG. 1a. Inner wall portion 37d may be of frustoconical shape, of an angle to match the frustoconical angle of the outer wall of male luer 36d, so that a luer-type connection is achieved when the components 16d, 34d are brought together as shown in FIG. 6. Because of the increased length of inner wall 37d, the end 90 of male luer 36d does not enter the lumen of flexible tubing 12d to a significant extent, and the added frustoconical retention seal at inner wall 37d is provided substantially completely by the engagement between inner wall 37d and the outer wall of male luer 36d in the manner of a luer connector seal. Thus, this arrangement provides a double seal: the seal between wall 37d and male luer 36d and the seal between male luer 36d and elastomeric wall 20d. Also, threaded retention ring 20d is retained in locked relation by screw threads 92 of housing 16d.

Figure 7:
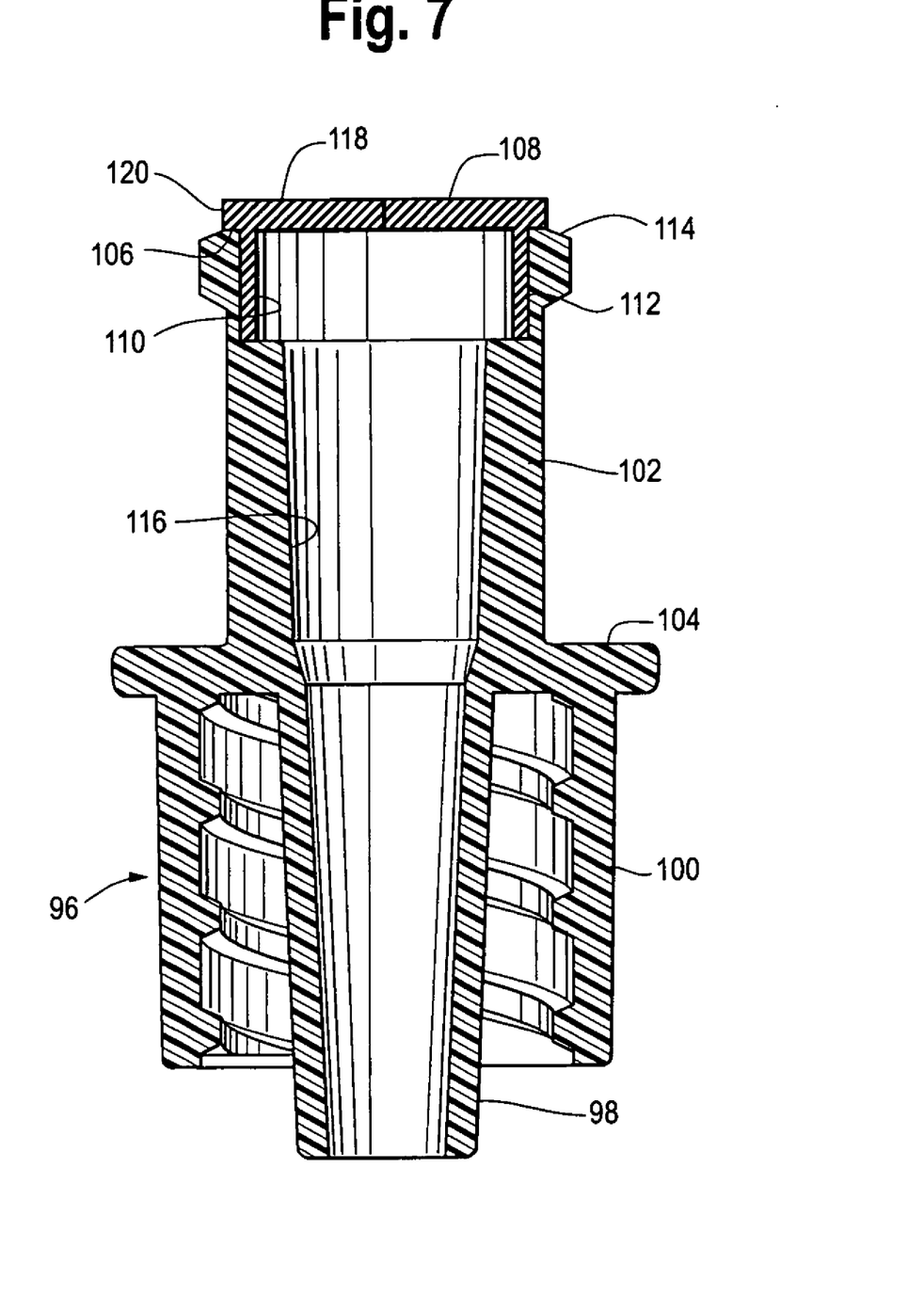
FIG. 7 is a longitudinal, sectional view of a luer-lock connector embodiment of this invention.

Referring to FIG. 7, in this embodiment an ISO standard male luer lock connector 96 has been modified as shown. A male luer 98 is surrounded by a threaded locking sleeve 100. An upstanding tube member 102 is carried on an end wall 104 of locking sleeve 100, and terminates in an annular seat 106 for an elastomeric wall 108 having a central perforation in a manner similar to previous embodiments. Also, elastomeric wall 108 defines a depending, tubular skirt 110, which may be optionally present to improve the sealing and anchoring of elastomeric wall 108 at the outer end of tube 102. Elastomeric wall 108 may be glued in place at annular seat 106, and additional strength of retention may be provided by further gluing at the area between sleeve 110 and the inner wall 112, which defines an expanded bore portion, to receive the deflected elastomeric wall 108 when a male luer or the like penetrates it to achieve fluid flow connection through elastomeric wall 108.

Ears 114 are provided for locking with a male luer lock connector sleeve in conventional manner.

Bore 116 of upstanding tube 102 may be of frustoconical shape in the manner of a female luer, for locking and sealing engagement with a male luer.

Thus, a male luer, or a male luer connector, may pass through elastomeric wall 108 in a manner similar to that previously described and enter into locking, sealing engagement in tapered bore 116. Then, that connected system may be further connected to a female luer lock connector That which is claimed is:

1. A medical device having an interior for containment of fluids; an opening into the interior, and an elastomeric wall having at least one perforation, said wall being essentially free of longitudinally inwardly extending projections and comprising a fixedly placed, flexible barrier across said opening, said wall further having an outer face that is entirely exposed to the exterior; said device also defining a passageway extending inwardly from adjacent to said elastomeric wall, said passageway being proportioned to receive and form an annular seal with a connector tube that is extended into said interior through said perforation.

2. The device of claim 1 in which the outer face of said elastomeric wall is laterally exposed to the exterior, to permit lateral swabbing for aseptic cleaning prior to use.

3. The device of claim 1 in which said device defines a bore portion positioned between said elastomeric wall and the passageway, said bore portion having an inner diameter larger than any inner diameter of said passageway, to provide a chamber that receives material of said elastomeric wall when a connector tube is extending through said perforation.

4. The device of claim 1 in which a connector tube penetrates said perforation and forms said annular seal with a frustoconical wall of said passageway, said connector tube having a frustoconical outer wall with an angle to substantially match said frustoconical passageway wall, to facilitate said annular seal.

5. The device and connector tube of claim 4 in which the connector tube comprises a male luer of an ISO standard male luer lock connector.

6. The device and connector tube of claim 5 in which said device defines outer lugs which are in connection with an outer locking sleeve of said ISO standard male luer lock connector.

7. The device of claim 1 which is in connection with a length of flexible tubing.

8. The device of claim 1 which comprises a female luer lock connector.

9. The device of claim 1 in which said perforation extends completely through said etastomeric wall.

10. The device of claim 9 in which said elastomeric wall is cut from an extruded elastomer sheet.

11. The device of claim 1 in which said elastomeric wall is cut from an extruded elastomer sheet.

12. A medical device having an interior for containment of fluids; an opening into the interior; an elastomeric wall having an outer surface and at least one perforation, said wall being essentially free of longitudinally inwardly extending projections and comprising a fixedly placed, flexible barrier across said opening, said wall further having an outer face that is entirely exposed to the exterior; said device also defining a passageway extending inwardly from a position adjacent to said elastomeric wall, said passageway having a frustoconical wall, to receive and form an annular seal with a connector tube that is extended into said interior through said perforation.

13. The device of claim 12 in which the outer face of said elastomeric wall is laterally exposed to the exterior, to permit lateral swabbing for aseptic cleaning prior to use.

14. The device of claim 12 in which said device defines a bore portion positioned between said elastomeric wall and the passageway, said bore portion having an inner diameter larger than any inner diameter of said passageway, to provide a chamber that receives material of said elastomeric wall when a connector tube is extending through said perforation.

15. The device of claim 12 in which a connector tube penetrates said perforation and forms said annular seal with the frustoconical passageway wall, said connector tube having a frustoconical outer wall with an angle to substantially match said frustoconical passageway wall, to facilitate said annular seal.

16. The device and connector tube of claim 15 in which the connector tube comprises a male luer of an ISO standard male luer lock connector.

17. The device and connector tube of claim 16 in which said device defines outer lugs which are in connection with an outer locking sleeve of said ISO standard male luer lock connector.

18. The device of claim 12, which is in connection with a length of flexible tubing.

19. The device of claim 12 which comprises a female luer lock connector.

20. The device of claim 12 in which said perforation extends completely through said elastomeric wall.

21. The device of claim 20 in which said elastomeric wall is cut from an extruded elastomer sheet.

22. The device of claim 12 in which said elastomeric wall is cut from an extruded elastomer sheet.

* * * * *